United States Patent [19]

Funakoshi et al.

[11] Patent Number: 5,391,711
[45] Date of Patent: Feb. 21, 1995

[54] BIOTINYLATING REAGENT AND PURIFICATION PROCESS FOR SYNTHESIZED PEPTIDE USING THEREOF

[75] Inventors: Susumu Funakoshi, Otsu; Hiroyuki Fukuda, Toyonaka, both of Japan

[73] Assignee: Nihan Millipore Kabushiki Kaisha, Yamagata, Japan

[21] Appl. No.: 37,777

[22] Filed: Mar. 26, 1993

[30] Foreign Application Priority Data

Jun. 4, 1992 [JP] Japan .................. 4-168218

[51] Int. Cl.$^6$ .............................................. A61K 37/02
[52] U.S. Cl. .................... 530/344; 530/345; 530/333; 530/334; 530/337
[58] Field of Search ............... 530/344, 345, 333, 334, 530/337

[56] References Cited

PUBLICATIONS

Funakoshi *J. Chromatogr* 638, 21 (1993).
D. R. Gretch, et al., "The Use of Biotinylated Monoclonal Antibodies and Streptavidin Affinity Chromatography to Isolate Herpesvirus Hydrophobic Proteins
(List continued on next page.)

*Primary Examiner*—Robert J. Hill, Jr.
*Assistant Examiner*—David Lukton
*Attorney, Agent, or Firm*—Hamilton, Brook, Smith & Reynolds

[57] ABSTRACT

This invention relates to a biotinylating reagent being used in purification process for synthesis mature peptide. The reagent has at one terminus a functional group capable of forming a bond with the N-terminus amino group of the mature peptide. The bond is stable to the final deprotection reaction under acidic condition at the post-synthesis step of the peptide synthesis process while the bond is specifically cleaved under a difined condition such as basic condition. The reagent also has at the other terminus a biotinyl group. The biotinyl-avidin coupling is used when the reagent modified mature peptide are immobilized selectively on avidin-agarose column. The compounds having following formula (II) are preferable as the reagent.

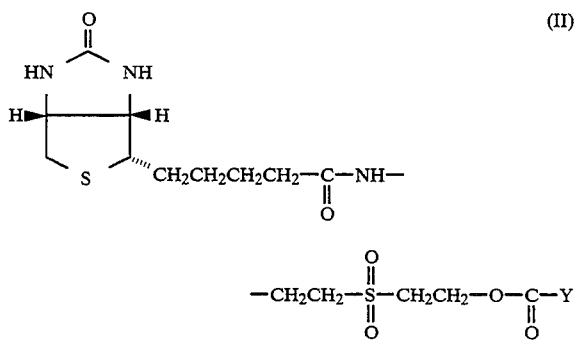

wherein Y is one of

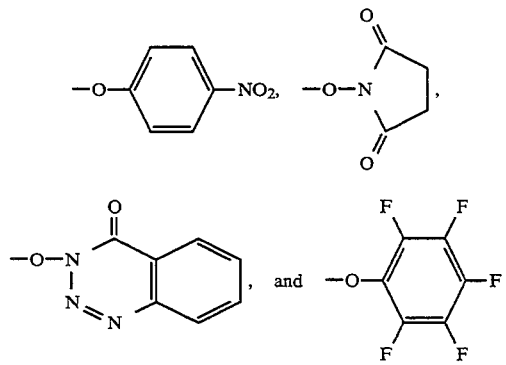

6 Claims, 2 Drawing Sheets

PUBLICATIONS or Glycoproteins", *Analytical Biochemistry,* 163:270–277 (1987).

D. E. Krieger, et al., "Affinity Purification of Synthetic Peptides", *Proc. Natl. Acad. Sci. USA,* 73(9):3160–3164, (1976).

T. J. Lobl, et al., "On-Resin Biotinylation of Chemically Synthesized Proteins for One-Step Purification", *Analytical Biochemistry,* 170:501–511 (1988).

C. A. Mouton, et al., "A Reagent for Covalently Attaching Biotin to Proteins Via a Cleavable Connector Arm", *Archives of Biochemistry and Biophysics,* 218(1):101–108 (Oct. 1, 1982).

M. Shimkus, "A Chemically Cleavable Biotinylated Nucleotide: Usefulness in the Recovery of Protein-DNA Complexes from Avidin Affinity Columns", *Proc. Natl. Acad. Sci. USA,* 82:2593–2597 (May 1985).

N. M. Green "Avidin 3. The Nature of the Biotin-Binding Site", *Biochem. J.,* 89:599 (1963).

N. M. Green and E. J. Toms "The Properties of Subunits of Avidin Coupled to Sepharose", *Biochem. J.,* 133:698–700 (1973).

N. Fujii, et al., "Studies of Peptides CLV. Evaluation of Trimethylsilyl Bromide as a Hard-Acid Deprotecting Reagent in Peptide Synthesis", *Chem. Pharm. Bull,* 35(9):3880–3883 (1987).

S. Funakoshi, et al., "A Modified Benzhydrylamine as a Handle Reagent for the Solid Phase Synthesis of Peptide Amides Based on the Fluorenylmethoxycarbonyl Method" *J. Chem. Soc. Chem. Commun.,* 383–384 (1988).

G. J. Tesser and I. C. Balvert-Geers, et al., "The Methylsulfonylethyloxycarbonyl Group, A New and Versatile Amino Protective Function", *Int. J. Peptide Protein Res.,* 7:295–305 (1975).

J. Diaz, "A Large-Scale Synthesis of Somatostatin for Clinical Use by a Novel Alternating Solution/Solid-Phase Procedure", *Bioorganic Chemistry* 8:429–442 (1979).

Merck Index, 11th Edition, p. 4472 (1989).

BIOTINYLATING REAGENT AND PURIFICATION PROCESS FOR SYNTHESIZED PEPTIDE USING THEREOF

BACKGROUND OF THE INVENTION

The present invention relates to a biotinylating reagent used in a purification procedure for synthesized peptide or proteins. The present invention will be a useful technique for making a pharmaceutical or a physiologically active agent.

Peptides and proteins are biological molecules existing normally in organisms. The elucidation of physiological activities and of mechanisms of these biological molecules are of much interest in the fields of biochemistry, physiology and medicine.

The synthesis of peptides or proteins having specific amino acid sequences has recently been made convenient the use of automated peptide synthesizers. Research in the above mentioned fields is expected to show much progress, if the synthesized peptides or proteins having specific amino acid sequences are provided with higher purities. However, the known peptide synthesis methods produce relatively large amounts of impurities in addition to the target compound. Therefore the most pressing objective of the solid-phase peptide synthesis method is to efficiently separate the target peptide from impurities in high yield (Analytical Biochemistry Vol. 170, p501, (1988)).

Gel filtration, high-performance liquid chromatography, or the combination thereof have been used for the purification of peptides or proteins synthesized by a solid-phase method (R. B. Merrifield, J. Am. Chem. Soc., 85, 2149 (1963)). Regarding some kinds of special peptides, affinity chromatography may be an effective purification method, but not a perfect one. The reason is that various amino acid deleted peptides may have an affinity (even a low degree) for the supports used in chromatography, the amino acid deleted peptides being synthesized as Impurities during the solid-phase synthesis and being in the resultant peptide mixture.

The solid-phase synthesis of peptides is made by a stepwise elongation. For example, in the case of the preparation of a 50 residue peptide wherein each condensation reaction has a yield of 99%, the overall synthetic yield approaches 60%. However, condensation reaction yields over 99% can not always be achieved because the condensation reaction depends on the sequence of the target peptides. As a result, amino acid deleted peptides accumulate as impurities derived from incomplete condensation reactions.

A capping by acetic anhydride is performed after every condensation reaction to terminate further elongation of peptide chains of non-target sequence and to avoid further production of amino acid deleted peptides. This procedure produces the effect that only the peptide having the target amino acid sequence has a free amino group at its N-terminus after the coupling of the final amino acid.

Several reports on the purification methods with use of the N-terminus amino group have been published (See, for example, T. J. Lobl, R. M. Deibel, and A. W. Yen, Anal. Biochem., 170, P.502 (1988)).

Another method has been developed in which the target peptide alone is absorbed and separated with a phenyl mercury column by attaching cysteine-methionine to the N-terminus of the synthesized target peptide, and using the SH group of the bound cysteine. Subsequent to the separation, the methionine-peptide bond is cleaved by BrCN to yield the target peptide (D. E. Krieger. B. W. Erikson, and R. B. Merrifield, Proc. Natl. Acad. Sci. U.S.A., 73, P.3160 (1976)). This method has a limitation of not being applicable to peptides containing methionine.

However, none of aforesaid methods has been able to achieve effective one-step separation. Instead they have required complicated processes.

The method of Lobl et al. selectively cleaves the t-BOC group as a protection group for the amino terminus of the target peptide synthesized on the solid support by using TFA/DCM, which is followed by washing with water, neutralizing, and washing with DCM and with DMF. The resulting peptide in a state of being protected with another functional group is then suspended in DMF. To the suspension, NHS-biotin (N-hydroxy succinimide biotin) is added in order to biotinylate the N-amino terminus of peptide. By using "low/high" HF, the biotinylated peptide is separated from the solid-phase support. The resultant mixture containing the biotinylated peptide is powdered by using ether, extracted with 6M guanidine-HCl buffer, and twice concentrated by dialysing. The resultant concentrate is passed through an avidin immobilized solid support such as avidin-agarose column (Pierce Co., Ltd.) in order to capture selectively the biotin-modified target peptide thereon. The biotin-modified target peptide can be eluted from the avidin immobilized solid support by using 0.1M guanidine-HCl (pH2.0). Thus, the method of Lobl et al. is no more than a separation method for a biotin-modified peptide or protein. It can never isolate the target peptide in its inherent or unmodified form, since there is no way for cleaving the biotin-peptide linkage selectively.

Improved methods are also known where NHS-SS-biotin (sulfosuccinimidyl 2-(biotin amide)ethyl-1,3-dithiopropionate) is used in place of NHS-biotin. After selective collection of the biotinylated peptide with an avidin-immobilized solid support, the SS bond of the reagent is broken by thiol so as to obtain the target peptide. However, the resulting peptide still contains an SH group residue from the reagent (See for example, Mouton C. A., et al. (1982) Arch. Biochem. Biophys. 218, 101–108; Shimkus, M., Levy, T. and Herman, T. (1985) Proc. Natl. Acad. Sci. (USA) 82, 2593–2597; Gretch, D. R, Suter, M. and Stinski, M. F. (1987) Anal. biochem. 163, PP.270–277).

SUMMARY OF THE INVENTION

Therefore, this Invention aims at providing a new biotinylating reagent and a purification process for synthesized peptides using the same. This invention also aims to provide a biotinylating reagent which is able to separate the mature target peptide selectively from the final mixture obtained by a solid-phase peptide synthesis, the separation being due to an avidin-biotin linkage, and which contributes to ultimately isolating the mature peptide unmodified, and a purification process using this reagent. A further objective of this invention is to provide a biotinylating reagent by which a synthesized peptide can be purified by a simple procedure having a high yield, and a purification process using the same. Still another objective of this invention is to provide a biotinylating reagent which can be applied to the purification of high molecular weight peptides or proteins.

The above objectives are achieved by a biotinylating reagent according to this invention, the reagent being used in the purification process where a mature target peptide having a free amino group at the N-terminus is selectively separated from a mixture of the mature peptide and end-capped immature peptides. The reagent is characterized by having at one terminus a functional group which is able to form a bond with the N-terminus of the mature peptide, the bond being stable to the final deprotection reaction under an acidic condition at the post-synthesis step of the peptide synthesis process and being specifically cleaved under a defined condition. The reagent is also characterized by having at the opposite terminus a biotinyl group.

Preferable examples of the biotinylating reagent according to this invention include compounds represented by following structural formula (II):

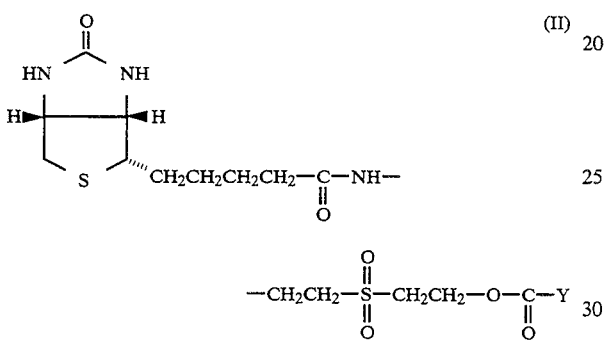

wherein Y is one of

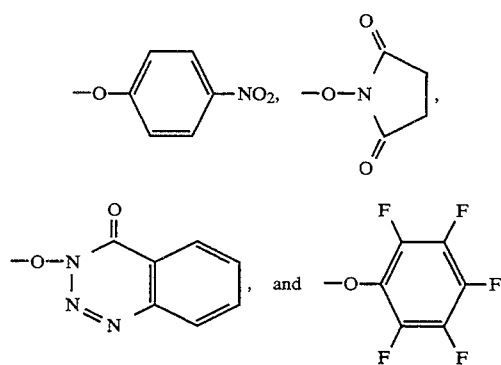

The biotinylating reagent of the formula (II) can be easily obtained when a compound represented by the following structural formula (I) is used as precursor.

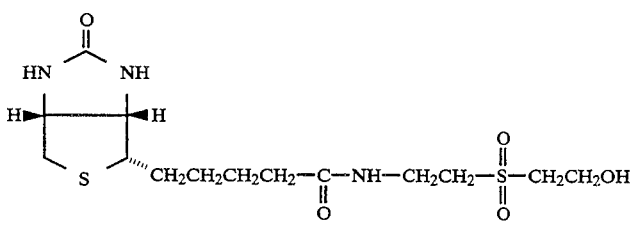

This invention is also embodied by a purification process for synthesized peptides where a mature target peptide having a free amino group at the N-terminus is selectively separated from a mixture of the mature peptide and end-capped immature peptides, and which is characterized by adding to the mixture the biotinylating reagent of aforementioned formula (II) in order to allow the carbonate terminus of the reagent to react with the free N-terminus amino group of the mature peptide, thereby selectively coupling the mature peptide at its free N-terminus amino group to the biotin containing residue of the biotinylating reagent.

A preferable purification process of this invention may include:

a) after introducing the final amino acid for a solid-phase peptide synthesis, the biotinylating reagent of the formula (II) is added to a first solid support to which both the mature peptide having a free N-terminus amino group at one terminus and the end-capped immature peptide have been bound, thereby selectively modifying the mature peptide with the reagent;

b) subjecting the first solid support to a first acidic condition so as to dissociate the mature peptide and immature peptides(s) from the first solid support;

c) contacting the resultant freed peptide mixture of above step b) with a second solid support having an avidin immobilized thereon so as to allow the biotinyl group of the residue from the biotinylating reagent to bind with the avidin, the residue from the biotinylating reagent having been coupled to the mature peptide at one terminus of the residue and the biotinyl group being at the other terminus of the residue, thereby capturing the modified mature peptide onto the second solid phase;

d) exposing the second solid support immobilized with the mature peptide of above step c) to a second acidic condition so as to cleave the avidin-biotinyl linkage, thereby separating the mature peptide modified with the biotin containing residue of the biotinylating reagent (hereinafter referred to as "biotinylated peptide") from the second solid support; and e) exposing the freed modified mature peptide to a specific condition under which the urethane linkage can be cleaved, thereby separating the mature peptide from the residue from the biotinylating reagent.

The purification method using the reagent of the present invention can isolate the target peptide in its unmodified and pure form from the peptide mixture with high speed and high yield. Further, the process is simple, and is performed without enduring troublesome washing steps. Therefore, the present method will make many contributions to the elucidation of physiological activities and mechanisms of peptides or proteins, and bring about progress in the synthesis of peptides and proteins.

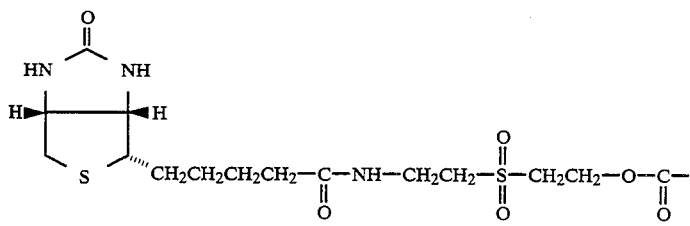

and

Figure 2:
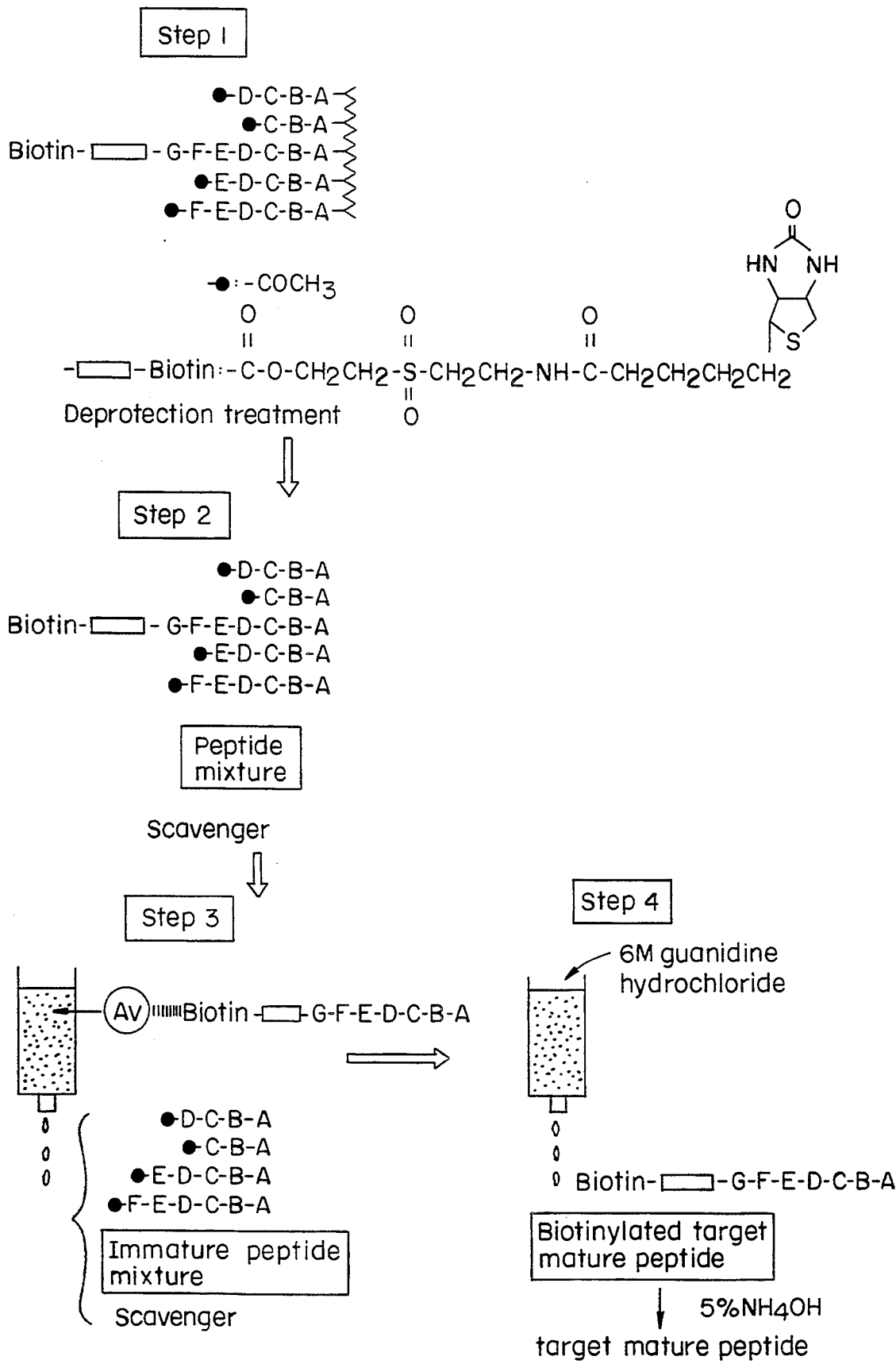

FIG. 2 is a flow chart showing the steps of peptide synthesis, bonding of the biotinylating reagent to the peptide, and purification steps with use of the avidin immobilized solid support.

DETAILED DESCRIPTION OF THE INVENTION

The present invention is hereby described in detail.

Figure 1:
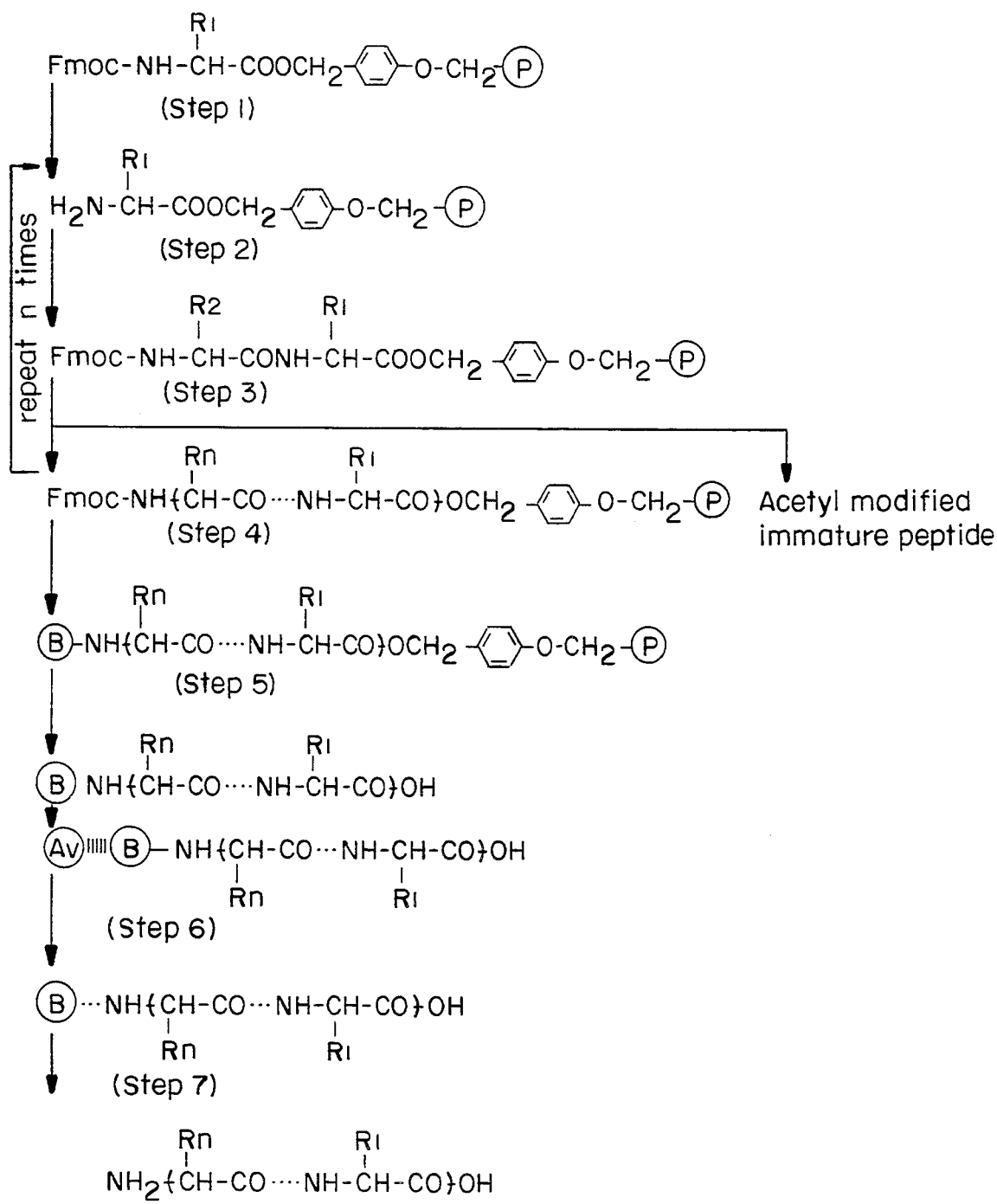
FIG. 1 is a flow chart showing peptide synthesis by the Fmoc solid-phase method and the following purification of the mature peptide Step 1 is the elimination of the 9-fluorolenylmethyloxycarbonyl (Fmoc) group by 20% piperdinedimethylformamide (DMF). Step 2 is a coupling reaction using Fmoc-NH—CH(R²)—COOH where R is a side chain group (NH₂—) and di-isopropylcarbodimide (DIPCDI)+N-hydroxybenzotriazole (HOBT) condensation agent or benzotriazole-1-yl-oxy-tris (dimethyl(amino)-phosphonium hexafluorophosphate (BOP)+HOBT condensation agent or pentafluorophenyl (PFP) ester. Step 3 is a capping reaction with acetic anhydride/pyridine; acetylation of remaining amino group. Step 4 is the elimination of Fmoc group by 20% piperdine/DMF and bonding of biotinylating reagent. Step 5 is a deprotection treatment. Step 6 is performed by contacting with an avidin immobilized agarose column (AV). Step 7 is the elution from avidin-agarose column with 6M quanidine hydrochloride and cleavage of biotinylating reagent from the peptide with 5% NH₄OH. Resin beads of the solid phase support are represented by P, and B corresponds with the following formula.

FIG. 1 illustrates an embodiment of the method according to this invention for purifying peptides prepared by the Fmoc (9-fluorenylmethyloxycarbonyl) method of solid-phase synthesis.

Peptide synthesis, as shown in FIG. 1, is made by the repetition of step 1 to step 3 in the conventional manner. Step 1 involves N-terminus Fmoc blocked first amino acid residues which are bound to solid support beads P. The support beads P are put into a reaction column of a peptide-synthesizer, where the mixed solution of 20% piperidine and dimethylformamide (DMF) is added in order to deprotect the N-terminal Fmoc group.

Step 2 involves adding an N-terminal Fmoc blocked second amino acid

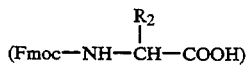

and a condensation agent to the column in order to bond the second amino residue group by means of a peptide bond to the first amino acid, which is bound to the support beads P; As a condensation agent, N,N'-diisopropylcarbodiimide. (DIPCD)+N-hydroxybenzotriazole (HOBT), Benzotriazole-1-yl-oxy-tris(dimethylamino)-phosphonium hexafluorophoshate (BOP)-+HOBT, or Pentafluorophenylester of these amino acids+HOBT are used.

Step 3 involves: The chains of the first amino acid that are not bound to the second amino acid should not be elongated in further synthetic steps; therefore, a mixture of acetic anhydride/pyridine is added to the column to let the N-terminus of non-reacted chains end-cap by acetyalating. On the support beads there are two types of peptide chains, i.e., one group is that of the first and the second amino acid residues bound together whose N-terminus is protected by an Fmoc group, and the other is that of the first amino residue whose N-terminus is bound to an acetyl group.

The process continues back to step 1. The N-terminal Fmoc group of the chains in which the first and the second amino residues are bound together is deprotected. As in step 2, the third amino acid and the condensation agent are added to let the third one bond to the second. The end-capping, as in step 3, is made to the chains where the third one is not bound. The processing through from step 1 to step 3 repeats till targeted n groups of amino acids are bound.

After the coupling of the final amino acid, two types of peptides are bound to the solid support (solid support beads P), namely, the mature target peptide having an amino group at the N-terminus, and the immature peptides whose N-terminus are modified by an acetyl-group from the capping with acetic anhydride. The target peptide is thus mixed with many kinds of impurities.

FIG. 1 describes the method to end-cap the terminus of immature peptides with an acetyl group. However, any kind of capping reagent can be used for the capping of the termini of immature peptides, if the capping is effective. Examples of suitable capping groups include propionyl, 4-nitrophenyl, 2,4-dinitrophenyl, or 2,6-dinitrophenyl group.

In the present invention for the purification of synthesized peptides, a biotinylating reagent is added to the solid support after the coupling of the last amino acid. The reagent should have a functional group at one terminus, which forms a bond with the free N-terminus of the mature peptide, which is stable under the acidic condition of the final deprotection reaction and clearable specifically under other conditions such as basic conditions. The linker should also have a biotinyl group capable of binding with avidin at the other terminus.

As the biotinylating reagent of this invention, compounds represented by the following stractural formula (II) are included:

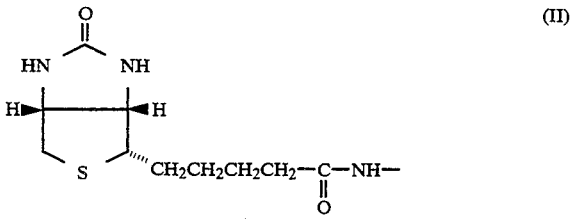

-continued

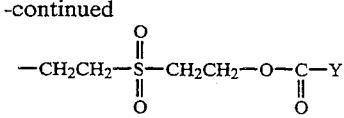

wherein Y is one of

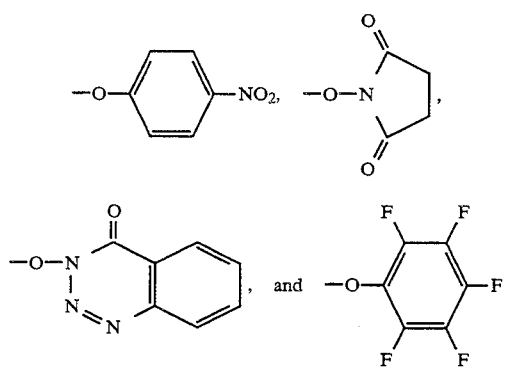

The compound (II) can be easily obtained from the precursor 2-[(N-biotinyl)-aminosulfonyl] ethanol. The compound is represented by the following structural formula (I) and is obtained from the reaction of 2-(aminoethyl sulfonyl) ethanol HCl with MHS-biotin (N-hydroxysuccinimide-biotin) in the presence of an organic basic catalyst such as tertiary amine.

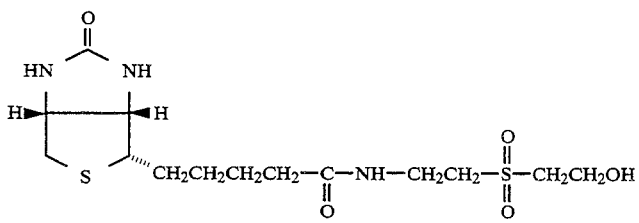

(I)

Compound (II) may be obtained by allowing the 2-[(N-biotinyl)-aminosulfonyl]ethanol to react with p-nitrophenyl chloroformate, N-hydroxysuccinimide, pentafluorochlorformate, or the like in pyridine.

When the biotinylating reagent mentioned above is added, as explained in FIG. 1, the reagent will only couple with the mature target peptide because only the mature peptide has the free-N-terminal amino group. 2-[(N-biotinyl)aminoethyl sulfonyl]-ethyloxycarbonyl group is thereby introduced to the N-terminus of the mature peptide.

Successively by the conventional method, the final deprotection reaction is carried out under acidic condition using reagents such as trimethylsilylbromide (TMSBr)-thioanisole/trifluroacetic acid. 2-[(N-biotinyl-)aminoethylsulfonyl]ethyloxycarbonyl-peptide, namely the mature peptide coupled to the reagent residue (hereinafter, referred to as "biotinylated peptide") and the immature peptides endcapped, for example by an acetyl group, thereby are cleaved from the solid support. The residue from the biotinylating reagent 2[-N-biotinyl-)aminoethylsulfonyl]-ethyloxycarbonyl group is stable, maintaining the bound state to the N-terminus of the mature peptide in the final deprotection reaction as explained before.

Then, the resultant mixture containing the biotinylated peptide and immature peptides is applied to another solid phase containing immobilized avidin at near neutral condition.

Preferably this solid phase containing immobilized avidin is maintained at around pH=7-9 by washing the solid phase with an inert buffer so as not to disturb the expected reaction. More preferably, a denaturing agent such as guanidine hydrochloride or urea is added in order to increase the solubility of the peptides.

As an example, PBS(-) buffer (ph=7.2) is used. Guanidine hydrochloride of 4-7 mol, preferably ca.6M guanidine hydrochloride, or urea of 4-8M, preferably ca.6M urea is used as a denaturing agent. Other buffers and denaturing agents can be used case-by-case.

By the above step, the selective immobilization of the biotinylated peptide to the second solid support can be attained by avidin-biotinyl linkage. The immature peptides and scavengers used for the deprotection will be passed through the second solid support column without being immobilized to the solid support. The next washing process of the solid support using a buffer such as PBS(-) easily removes the remaining immature peptides and scavengers from the column.

The resultant biotinylated peptide complex with avidin immobilized solid support is exposed to an acidic condition such as 6M guanidine-HCl (pH1.5) in order to separate the biotinylate peptide from the avidin immobilized solid support.

Finally, the resultant solution of freed biotinylated peptide is exposed to a specific condition, such as a basic condition, which causes the cleavage of the urethane linkage formed between the biotin containing residue of the biotinylating reagent and the mature peptide, thereby cleaving the target mature peptide from the biotinylating reagent residue. If 5% ammonium solution is used for this basic treatment, some peptides which are not dissolved in 5% NH$_4$OH may remain as precipitates in the receiver. If the 5% ammonium treatment is followed by treatment with 50% acetic acid, the precipitates can be dissolved and recovery of the target mature peptide become efficacious. The resultant mixture of the mature peptide and the biotinylating reagent residue having the biotinyl group cleaved from the mature peptide are applied to a reversed phase high performance liquid chromatography (RPHPLC) or a gel filtration separation as a conventional technique, in order to isolate the mature peptide.

FIG. 2 is a flow-chart showing one embodiment of the peptide purification method of the present invention. In this figure the mature target peptide is shown as G-F-E-D-C-B-A; C-B-A, D-C-B-A-, E-D-C-B-A and F-E-D-C-B-A are impurities. Step 1 of FIG. 2 shows the targeted mature peptide mixed with many impurities. Both the mature peptide having a free N-terminal amino group and immature peptides (impurities) having an acetyl-group modified terminus by end-capping with acetic anhydride are bound to the solid support (solid support beads). The biotinylating reagent of the present invention, as shown in Structural Formula II selectively bonds only to the terminus of the mature peptide G-F-E-D-C-B-A. The final deprotection treatment in the peptide synthesis method cleaves the target peptide and immature peptides from the solid support, as shown in step 2. The next process shown in step 3 involves allowing the mixture of the biotinylated peptide and immature peptides to come in contact with an avidin-agarose column. Only the mature peptide adheres to the column by virtue of the avidin-biotinyl reaction, and immature peptides and other reagents are eluted from the column. Step 4 involves exposing the column to acidic conditions under which the avidin-biotinyl bond is selectively cleaved, thereby eluting the biotinylated peptide from the avidin-agarose column. Step 5 involves exposing the biotinylated peptide to a basic condition under which the bond between the biotin containing residue of the biotinylating reagent and the mature peptide G-F-D-C-B-A is selectively cleaved.

EXAMPLES

The present invention is described in more detail with the experimental examples described below. However, it will be understood that the present invention is not limited to these few disclosed examples.

EXAMPLE 1

Synthesis of Compound e (precursor for biotinylating reagent)

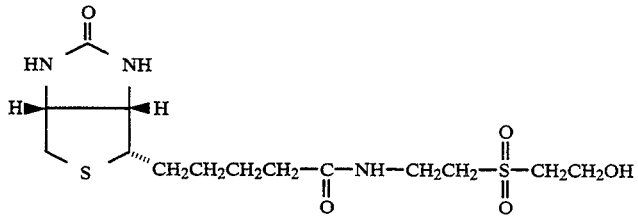

2-[N-(p-methyoxybenzyloxycarbonyl)-aminoethylsulfonyl] ethanol was synthesized in accordance with the procedures 1-1 to 1-3 of Example 1, or the procedures 2-1 to 2-3 of Example 2 disclosed in WO92/06107. The associated portion of this reference are incorporated herein.

6.35 g (0.02 mol) 2-[N-(p-methyoxybenzycarbonyl)-aminoethylsulfonyl] ethanol was treated with 20 ml (4 equivalent) of 4N-HCl/dioxane for 1 hour in the presence of anisole (4.35 ml, 2 equivalent). After the reaction, HCl/dioxane was evaporated, and then dry-ether was added. The powder like residue obtained from a filtration was dried in a KOH desiccator under reduced pressure for 3 hours.

The resulting 2-aminoethylsulfonyl ethanol hydrochloride was suspended in DMF (200 ml). After addition of triethylamine (5.6 ml, 0.04 mol) and biotin N-hydroxysuccinimide ester (6.86 g, 0.02 mol), the solution was stirred for 4 hours. The filtrate obtained by a filtration of the reaction mixture was concentrated under reduced pressure to produce a concentrated dried solid. The concentrated dried solid was powdered by adding methanol and stirring thereafter. The crude product was recrystallized from methanol to obtain 4.07 g of purified crystal (yield 54%).

The specification of compound e obtained by the above was as follows: M.p.: 126°~127° C. Mass spectroscopy: $M+H^+=380.3$ (Mw: 379.5) $Rf_{8:3:1}=0.32$ (Solvent: Lower phase of $CHCl_3$—MeOH—$H_2O$ (8:3:1), TLC (E. Merck, Germany) The theoretical value of $C_{14}H_{25}N_3O_6S_2$ $\frac{1}{2}H_2O$: C=43.27;H=6.75;N=10.81 The measured value: C=43.59;H=6.63;N=10.96 NMR(DMSO-d$_6$): $\delta$1.36–1.23(m,2H'), 1.46–1.37(m,1H'), 1.56–1.46(m,2-H,I,I'), 1.68–1.56(m,1H), 2.07(t,J=7.4 Hz,2H), 2.58(d,J=12.4 Hz,1H,N), 2.82(dd,J=12.4 and 5.1 Hz,1H,M), 3.10(ddd,J=8.3,6.3 and 4.5 Hz, 1H), 3.28–3.21(m,4H), 3.49–3.41(m,2H), 3.78(t,J=5.8 Hz,2H), 4.13(dd,J=7.7 and 4.4 Hz, 1H), 4.31 (dd,J=7.7 and 4.3 Hz,1H), 6.45–6.35(m,2H), 8.00(t,J=5.7 Hz,1H).

EXAMPLE 2

Synthesis of Compound f (biotinylating reagent)

3.79 g (10 mmol) of Compound e obtained in Example 1 was dissolved in 30 ml of anhydrous pyridine. To the pyridine solution 2.02 g(10 mmol) of p-nitrophenylchloroformate was added with stirring at 0° C. The reaction solution was concentrated under reduced pressure after 5 hours stirring.

The produced concentrated residue was crystallized by the addition of 1N-HCl/ether. The crystals were isolated by filtration and then washed with water. The crude crystals were recrystallized from DMF/ethyl acetate to obtain 4.07 g of purified crystal (yield 75%).

The specifications of Compound f obtained by the above were as follows: M.p.: 104°~105° C. mass spectrometry: $M+H^+=545.3$ (Mw: 544.6) $Rf_{8:3:1}=0.37$ The theoretical value of $C_{21}H_{28}N_4O_9S_2 \cdot \frac{1}{2}H_2O$:

(I)

C=45.65;H=5.37;N=10.22 The measured value: C=45.75;H=5.22;N=10.08 NMR(DMSO-d$_6$): $\delta$1.36–1.23(m,2H), 1.47–1.37(m,1H), 1.58–1.46(m,2H), 1.67–1.55(m,1H), 2.05(t,J=7.3 Hz,2H), 2.57(d,J=12.4 Hz,1H), 2.81(dd,J=12.4 and 5.0 Hz,1H), 3.08(ddd,J=8.2,6.5 and 4.5 Hz, 1H,L), 3.32(t,J=6.9 Hz,2H,E), 3.48(q,J=6.7 Hz,2H), 3.68(t,J=5.7 Hz,2H), 4.11(ddd,J=7.8,4.5 and 2.0 Hz,1H), 4.29 (dd,J=7.8 and 5.2 Hz,1H,O), 4.62(t,J=5.7 Hz,2H), 6.33(br.s,1H),6.38(br.s,1H), 7.58(ddd,J=9.2,3.3 and 2.2 Hz,2H, aromatic H), 8.07(br.t,J=5.9 Hz,1H), 8.33(ddd,J=9.2,3.3 and 2.2 Hz,2H,aromatic H).

EXAMPLE 3

Purification of Synthesized Peptide

Polyphemusin II was synthesized and purified in order to clarify the availability of this purification method of the present invention. Polyphemusin II was synthesized by Fmoc-based solid-phase synthesis according to the procedure shown in FIG. 1, and purified. Polyphemusin II is a 18-residue peptide with C-terminus amide and two disulfide bonds. For the synthesis, Cys derivative whose thiol group was protected with Acm (acetoamidomethyl) was used. SEQ ID NO: 1: the C-terminus amide of Arg-Arg-Trp-Cys-Phe-Arg-Val-Cys-Tyr-Lys-Gly-Phe-Cys-Tyr-Arg-Lys-Cys-Arg wherein each cysteine has an S-acetamidomethyl group At the final step of the synthesis, Compound f prepared according to Example 2 (109 mg, 5 eq.) and N-Hydroxybenzotriazole (152 mg, 5 eq.) were added to the solid support resin (0.2 mmol), and then stirred in dimethylformamide (10 ml) for 2 hr. in order to introduce a 2-[N-biotinylaminoethylsulfonyl]ethyloxycarbonyl group to the N-terminus of Polyphemusin synthesized on the resin. Subsequently the deprotection of the solid phase resin (100 mg) was carried out at 0° C. for 2 hr. with a solution (10 ml) of 1M trimethylsilyl bromide (TMSBr)-thioanisole/trifluoroacetic acid (TFA) (each compound is present at concentrations of 1M) in the presence of ethanediol (0.2 ml) and m-cresol (0.5 ml) [N. FuJii, A. Otaka, N. Sugiyama, M. Hatano, and H. Yajima, Chem. Pharm. Bull., 35, 3880], then TMSBr and TFA were evaporated off, and diethyl ether was added to obtain the peptide as a powder. The resulting powder was dissolved in a (-)phosphate buffered saline[(-)PBS], pH=7.2(Nissui Seiyaku K. K., Japan). Subsequently the solution was introduced onto an avidin-agarose column (Pierce Co., Ltd.) which was pretreated with the same PBS, which is followed by washing the column with the buffer in order to immobilize biotinylated the mature peptide having biotinyl group selectively on the column while discharging the immature peptides out from the column.

6m guanidine hydrochloride (ph=1.5) was passed through the column to which the biotinylated peptide was attached in order to elute the biotinylated peptide from the column. To the eluate 28% $NH_4OH$ was added until the entire ammonium concentration of the eluate reaches 5% in order to cleave the mature peptide from the biotin containing residue of the biotinylating reagent (2-[N-biotinyl-adminoethylsulfonyl]oxycarbonyl group).

The resultant mixture of the mature peptide and the biotinylating reagent residue was applied to RPHPLC or gelfiltration in accordance with the teachings in this art in order to separate the mature peptide Polyphemusin II from the biotinylating reagent residue. Analysis of the purified Polyphemusin II thus obtained by HPLC showed a single peak.

The results of amino acid sequence analysis and FAB mass spectroscopy of the purified peptide agreed with the theoretical [Acm-Polyphemusin II:2714.1 (M+H+), calculated on $C_{120}H_{185}N_{41}O_{24}S_4$].

EXAMPLE 4

Purification of Synthesized Peptide

The present invention was employed for the synthesis of a protein, human Growth Hormone Releasing Factor (hGRF). hGRF was synthesized by Fmoc-based solid-phase synthesis according to the procedure Funakoshi et al., J. Chromatography, 638:21 (1993), and purified. hGRF is a 44-residue peptide. SEQ ID NO: 2: the C-terminus amide of Tyr-Ala-Asp-Ala-Ile-Phe-Thr-Asn-Ser-Tyr-Arg-Lys -Val-Leu-Gly-Gln-Leu-Ser-Ala-Arg-Lys-Leu-Leu-Gln-Asp-Ile-Met -Ser-Arg-Gln-Gln-Gly-Glu-Ser-Asn-Gln-Glu-Arg-Gly-Ala-Arg-Ala -Arg-Leu At the final step of the synthesis, the Compound f prepared according to Example 2 (109 mg, 5 eq.) and N-hydroxybenzotriazole (152 mg, 5 eq.) were added to the solid phase resin (0.2 mmol), and subsequently stirred in dimethylformamide (10 ml) for 2 hr. in order to introduce the 2-[N-biotinyl-aminoethylsulfonyl]ethyl-oxycarbonyl fragment to the N-terminus of hGRF synthesized on the resin. Deprotection was carried out at 0° C. for 2 hr. with 1M TMSBr-thioanisole/TFA (10 ml) In the presence of ethanediol (0.2 ml) and m-cresol (0.5 ml) (each component is present at a concentration of 1M). Following the deprotection, TMSBr and TFA were evaporated off, and diethylether was added to obtain the peptide as a powder. The resulting powder was dissolved in PBS, pH=7.2 (Nissui Seiyaku K. K., Japan). Subsequently the solution was introduced onto an avidin-agarose column (Pierce Co., Ltd.) which was pretreated with the same PBS, which is followed by washing the column with the buffer in order to immobilize the biotinylated peptide selectively on the column while discharging the immature peptides out from the column.

6M guanidine hydrochloride (pH=1.5) was passed through the column to which the biotinylated peptide was attached in order to elute the biotinylated peptide from the column. To the eluate 28% $NH_4OH$ was added until the entire ammonium concentration of the eluate reaches to 5% in order to cleave the mature peptide from the biotin containing residue of the biotinylating reagent (2-[N-biotinylaminoethylsulfonyl]ethyloxycarbonyl group).

The resultant mixture of the mature peptide and the biotinylating reagent residue was applied to RPHPLC or gelfiltration in accordance with the teachings in this art in order to separate the mature peptide hGRF from the biotinylating reagent residue. Analysis of the purified hGRF thus obtained by HPLC showed a single peak.

The results of amino acid sequence analysis and FAB mass spectroscopy of the purified peptide agreed with the theoretical [hGRF:5037.8 (M+H+), calculated on $C_{215}H_{358}N_{72}O_{66}S$].

---

What is claimed are:

1. A method of separating a mature peptide having an N-terminal amino group from a mixture comprising the mature peptide and one or more end-capped immature peptides, by selectively attaching a biotin-containing residue from a biotinylating reagent to the mature peptide, wherein the method comprises the steps of:

a) adding to said peptide mixture the biotinylating agent wherein said biotinylating agent has the following structure:

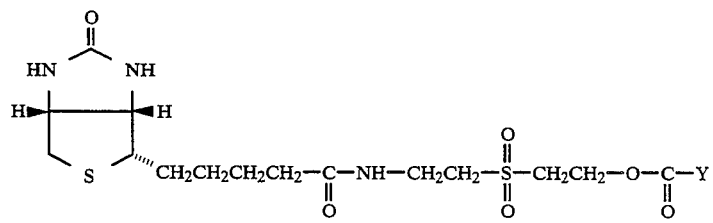

wherein Y is selected from the group consisting of

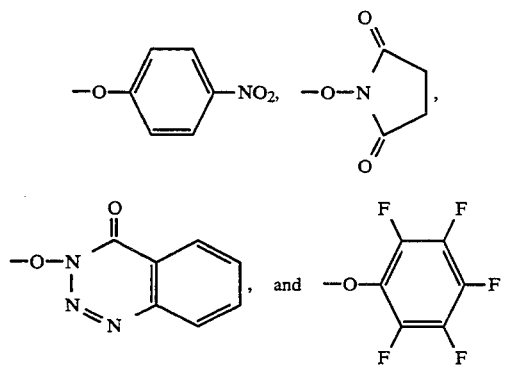

b) exposing the peptide mixture to the biotinylating agent whereby the Y substituent thereon is selectively displaced by the N-terminal amino group of the mature peptide, thereby forming a urethane linkage between the terminal amino group of the mature peptide and the biotin-containing residue from the biotinylating reagent;

c) separating the mature peptide by contacting the product of step (b) with a solid support containing an immobilized avidin moiety, to selectively capture the biotinylated mature peptide by forming a biotin avidin complex;

d) removing unbound immature end-capped peptides from the product of step (c);

e) dissociating the mature biotinylated peptide from the solid support under acidic conditions; and f) cleaving the biotin-containing residue from the mature peptide to form a mixture comprising mature peptide and biotin-containing residue.

2. A method of separating a mature peptide having an N-terminal amino group from a mixture comprising the mature peptide and one or more end-capped immature peptides, wherein the mature peptide and end-capped peptides are attached to a first solid support, comprising the steps of:

a) adding to said peptide mixture a biotinylating agent having the following structure:

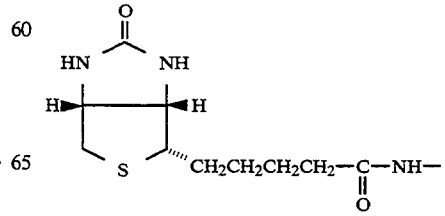

-continued

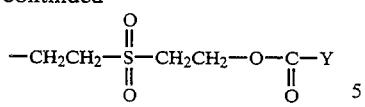

wherein Y is selected from the group consisting of

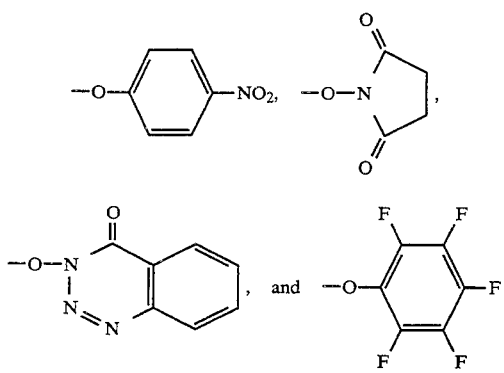

b) exposing the peptide mixture and the biotinylating reagent to conditions suitable for the biotinylating agent and the N-terminal amino group of the mature peptide to react so that the Y substituent thereon is selectively displaced by the N-terminal amino group of the mature peptide, thereby forming a urethane linkage between the terminal amino group of the mature peptide and the biotin-containing residue from the biotinylating reagent to form a biotinylated mature peptide;

c) cleaving the biotinylated mature peptide and the immature end-capped peptides from the first solid support under acidic conditions;

d) contacting the product of step (c) with a second solid support containing an immobilized avidin moiety, to selectively capture the biotinylated mature peptide by forming a biotin avidin complex;

e) removing unbound immature end-capped peptides from the product of step (d);

f) dissociating the mature biotinylated peptide from the second solid support under acidic conditions;

g) cleaving the biotin-containing residue from the mature peptide to form a mixture comprising mature peptide and biotin-containing residue; and h) separating the mature peptide from the mixture of step (g).

3. The method of claim 2 wherein step (h) is performed by subjecting the mixture of step (g) to reverse phase high pressure liquid chromatography or gel filtration.

4. The method of claim 2 wherein the biotinylated mature peptide and the end-capped immature peptides of step (c) are precipitated and resuspended in a buffer before being contacted with the second solid support containing immobilized avidin.

5. The method of claim 4 wherein the biotinylated peptide and the end-capped immature peptides are precipitated by the addition of ether.

6. The method of claim 2 wherein step d) is performed in the presence of a denaturing agent.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 18 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Arg Arg Trp Cys Phe Arg Val Cys Tyr Lys Gly Phe Cys Tyr Arg Lys

```
 1                   5                       1 0                      1 5
```

Cys Arg (2) INFORMATION FOR SEQ ID NO:2:

(i) SEQUENCE CHARACTERISTICS:
        (A) LENGTH: 44 amino acids
        (B) TYPE: amino acid
        (D) TOPOLOGY: linear (ii) MOLECULE TYPE: peptide (xi) SEQUENCE DESCRIPTION: SEQ ID NO:2:

```
Tyr Ala Asp Ala Ile Phe Thr Asn Ser Tyr Arg Lys Val Leu Gly Gln
 1               5                   1 0                      1 5

Leu Ser Ala Arg Lys Leu Leu Gln Asp Ile Met Ser Arg Gln Gln Gly
             2 0                  2 5                  3 0

Glu Ser Asn Gln Glu Arg Gly Ala Arg Ala Arg Leu
             3 5                  4 0
```